US005618976A

United States Patent [19]
Sandler

[11] Patent Number: 5,618,976
[45] Date of Patent: Apr. 8, 1997

[54] ALKANESULFONAMIDES FROM AMMONIUM ALKANESULFONATES

[75] Inventor: Stanley R. Sandler, Springfield, Pa.

[73] Assignee: Elf Atochem North America, Inc., Philadelphia, Pa.

[21] Appl. No.: 612,632

[22] Filed: Mar. 6, 1996

[51] Int. Cl.⁶ .................................................. C07C 303/36
[52] U.S. Cl. .................................................. 564/98; 564/99
[58] Field of Search ........................................ 564/98, 99

[56] References Cited

U.S. PATENT DOCUMENTS

| | | | |
|---|---|---|---|
| 4,970,339 | 11/1990 | Sandler et al. | 564/98 |
| 5,159,112 | 10/1992 | Ollivier et al. | 564/98 |
| 5,166,431 | 11/1992 | Sandler et al. | 564/98 |
| 5,455,377 | 10/1995 | Ronchi et al. | 564/98 |

*Primary Examiner*—Peter O'Sullivan

[57] ABSTRACT

A process is disclosed for the conversion of an ammonium or amine salt of an alkanesulfonic acid to its corresponding alkanesulfonamide by heating the salt to at least its melting point to remove the water by-product and recover an alkanesulfonamide.

5 Claims, No Drawings

ALKANESULFONAMIDES FROM AMMONIUM ALKANESULFONATES

BACKGROUND

This invention relates to a facile, thermal process for the preparation of alkanesulfonamides. More particularly, it concerns a process of heating an ammonium salt of an alkanesulfonic acid to a temperature of at least its melting point for a time sufficient to convert the salt to an alkanesulfonamide.

PRIOR ART

It is the current commercial procedure to prepare methanesulfonamide by the reaction of methanesulfonyl chloride with ammonia in the presence of an appropriate solvent, e.g., tetrahydrofuran. Ammonium chloride precipitates from the solvent and the solvent must then be recovered and recycled to operate at a reasonable cost. Examples of this earlier process are shown in U.S. Pat. Nos. 4,970,339; 5,159,112 and 5,166,431.

STATEMENT OF THE INVENTION

This invention is a process for the preparation of an alkanesulfonamide from an ammonium or amine salt of an alkanesulfonic acid by heating said salt to a temperature at least to its melting point up to about 450° C., and recovering a reaction product which is an alkanesulfonamide corresponding to said salt.

DETAILED DESCRIPTION OF THE INVENTION

The process of this invention is the thermal conversion of an ammonium or amine salt of an alkanesulfonic acid to a reaction product which is the corresponding alkanesulfonamide. The pure alkanesulfonamide reaction product is free of the ammonium or amine ions of the starting material from which it was derived.

The thermal process includes heating the salt to at least its melting point, generally about 300° C., up to about 450° C., for a reaction time sufficient to drive off water and obtain the sulfonamide product. Heating may be accomplished by any suitable means, e.g., oil bath, hot plate, heating mantle, heat gun, superheated steam jacket, microwave oven or other suitable means to heat the salt to its melting point and above. The preferred temperature range for the thermally induced reaction is between about 350° and 400° C.

The pressure of the reaction can be less than 1 atmosphere or above and is preferably established at between about 1 and 10 atmospheres (atm), more preferably between 1 and 5 atm.

The time of reaction is also not critical except that the salt must be exposed to the required temperature for sufficient time to obtain the sulfonamide product. Preferably, the time of reaction will range from about 10 to about 60 minutes, more preferably from about 10 to about 30 minutes depending on the reaction temperature and the starting salt employed.

In that the reaction may not proceed at either high yields or at low reaction conversions, recycle of the starting material may be employed as needed.

An advantage for the process of this invention is that no solvent is necessary to carry out the reaction to obtain the product. If a solvent is desired, particularly for the separation of the pure product from the crude, a pure sulfonamide (less than about 5%, preferably less than about 1% impurities) identical to the reaction product may be employed for extraction purification in an amount preferably less than 50 wt. %, more preferably less than 30 wt. %. Alternatively, one may use other solvents to extract salt impurities from the product including, e.g., ethanol, tetrahydrofurane, dimethylfurane, 1,3-dioxolane and the like.

While the alkanesulfonamides may be used as solvents in the process of this invention, they may also serve to act as catalysts to improve the reaction rate of the process.

The ammonium or amine salts of alkanesulfonic acids useful as starting materials in the process are represented by the following general formula:

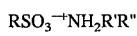

where R is $C_1$–$C_{20}$ alkyl, and R' and R" are the same or different substituents including hydrogen, $C_1$–$C_{20}$ alkyl or $C_6$–$C_{12}$ aryl groups. Examples of these starting materials include the ammonium salts of methanesulfonic acid, ethanesulfonic acid, propanesulfonic acid, hexanesulfonic acid, decanesulfonic acid, and octadecanesulfonic acid; the corresponding salts of alkanesulfonic acids where the ammonium ion is substituted with one or two alkyl groups, e.g., methyl amine, methylethylamine, dipropylamine, n-butylamine, cyclohexylamine, octadecylamine, methylethylhexylamine and the like are useful starting materials. The corresponding salts of alkanesulfonic acids where the ammonium ion is substituted with an aryl group are also included, e.g., methylbenzylamine salt of an alkanesulfonic acid.

If desired, mixtures of the starting materials may be used in the process to obtain mixed alkanesulfonamide products.

The following examples are set forth to demonstrate the process of this invention.

EXAMPLE 1

0.5 g of ammonium methanesulfonate was added to a 10 ml. test tube which was placed in a microwave oven [CEM Corp. MDS #2000, Mathews, N.C.] with an Erlenmeyer flask inverted over its top. These were set in a 4 dram vial which was placed in a 100 ml. glass beaker. After 11 minutes in the microwave oven, operating at a programmed temperature for a preset time, the sample melted and the melt was first clear and then became reddish. The sample gave off white vapors which condensed on the inverted Erlenmeyer. The residue (0.25 g) and the sublimed solids (0.25 g) were analyzed by proton nuclear magnetic resonance (NMR) and then by gas chromatography/mass spectroscopy (GC/MS). The NMR indicated a high concentration of methanesulfonamide in the sublimed solids. The structure was also confirmed by the GC/MS.

EXAMPLE 2

A 0.5 g sample of ammonium methanesulfonate (AMS) was added to a 9 dram vial and an inverted 25 ml beaker was placed over it. The sample in the vial was heated on a hot plate (300°–330° C.) to melt the AMS and cause it to vaporize. The vapors were condensed/sublimed onto the inverted beaker and then analyzed by NMR. The condensed/sublimed solids showed a strong $^1$H NMR singlet band at 3.40 ppm which was indicative of methanesulfonamide.

EXAMPLE 3

To a laboratory sublimation apparatus was added 1.0 gram of ammonium methanesulfonate (AMS). Then water was passed through the condenser/cold surface (top of apparatus) while the bottom of the apparatus was heated with a heat gun to melt the AMS and cause it to vaporize. The sublimed solids 0.15 g and the residue 0.64 g were analyzed by proton NMR which indicated methanesulfonamide was present in both samples (3% and 1%, respectively).

I claim:

1. A method of preparing alkanesulfonamides comprising heating at least to its melting point up to about 450° C. the ammonium or amine salt of an alkanesulfonic acid having the formula:

$$RSO_3^- {}^+NH_2R'R''$$

where R is a $C_1$–$C_{20}$ alkyl group, and R' and R'' are the same or different substituents including hydrogen, $C_1$–$C_{20}$ alkyl or $C_6$–$C_{12}$ aryl groups, and continuing said heating for a time sufficient to remove the water of reaction and to obtain a reaction product which is an alkanesulfonamide corresponding to said salt.

2. The method of claim 1 wherein the salt is the ammonium salt of methanesulfonic acid.

3. The method of claim 2 wherein the crude reaction product is purified by extraction in an amount of up to 50 weight percent pure methanesulfonamide.

4. The method of claim 1 wherein the salt is an amine salt of methanesulfonic acid.

5. The method of claim 1 wherein the reaction temperature is maintained by heating said salt in a microwave oven.

* * * * *